(12) United States Patent
McDonald

(10) Patent No.: US 7,284,983 B2
(45) Date of Patent: Oct. 23, 2007

(54) MATRIX BAND RETAINER

(75) Inventor: Simon Paul McDonald, Katikati (NZ)

(73) Assignee: Tri-Dent Innovations Limited, Bay of Plenty (NZ)

( * ) Notice: Subject to any disclaimer, the term of this patent is extended or adjusted under 35 U.S.C. 154(b) by 149 days.

(21) Appl. No.: 11/006,815

(22) Filed: Dec. 8, 2004

(65) Prior Publication Data

US 2005/0147941 A1    Jul. 7, 2005

(30) Foreign Application Priority Data

Dec. 8, 2003   (NZ) ...................... 530034

(51) Int. Cl.
*A61C 3/00* (2006.01)
*A61C 5/12* (2006.01)

(52) U.S. Cl. ...................... 433/153; 433/139

(58) Field of Classification Search ................ 433/153, 433/155, 139, 39, 149, 156, 162
See application file for complete search history.

(56) References Cited

U.S. PATENT DOCUMENTS

| | | | | |
|---|---|---|---|---|
| 1,908,145 A | * | 5/1933 | Harper | 433/158 |
| 4,007,530 A | * | 2/1977 | Gaccione | 433/139 |
| 4,718,852 A | * | 1/1988 | Galler | 433/148 |
| 6,220,858 B1 | * | 4/2001 | McKenna et al. | 433/39 |
| 6,293,796 B1 | * | 9/2001 | Trom et al. | 433/155 |
| 6,336,810 B1 | * | 1/2002 | Bertoletti | 433/39 |
| 6,609,911 B2 | * | 8/2003 | Garrison | 433/139 |
| 2002/0155410 A1 | * | 10/2002 | Bills | 433/153 |
| 2003/0059741 A1 | * | 3/2003 | Bills | 433/153 |

FOREIGN PATENT DOCUMENTS

| | | |
|---|---|---|
| CH | 387223 | 1/1965 |
| EP | 0097266 | 1/1984 |
| GB | 435004 | 9/1935 |

* cited by examiner

*Primary Examiner*—Cary E. O'Connor
(74) *Attorney, Agent, or Firm*—Jacobson Holman PLLC

(57) ABSTRACT

A matrix band retainer for dental restoration has a unitary member of a stiff planar spring material. The unitary member has an open ring substantially in a first plane, with the plane of the material of the ring perpendicular to the first plane. A tine at each end of the open ring extends substantially normal to the plane of the ring. Each tine has a first planar portion extending from the ring and a second planar portion extending from the first planar portion. The second planar portion is at an angle to the first planar portion and adjoins the first planar portion to define a ridge. The ridges of each tine face each other across a gap.

Each tine may be bifurcated at the end distal from the ring so that the distal portion of each of the first planar portion and the second planar portion are divided by a notch. A dental wedge can be inserted through the notch with the matrix band retainer in place.

21 Claims, 8 Drawing Sheets

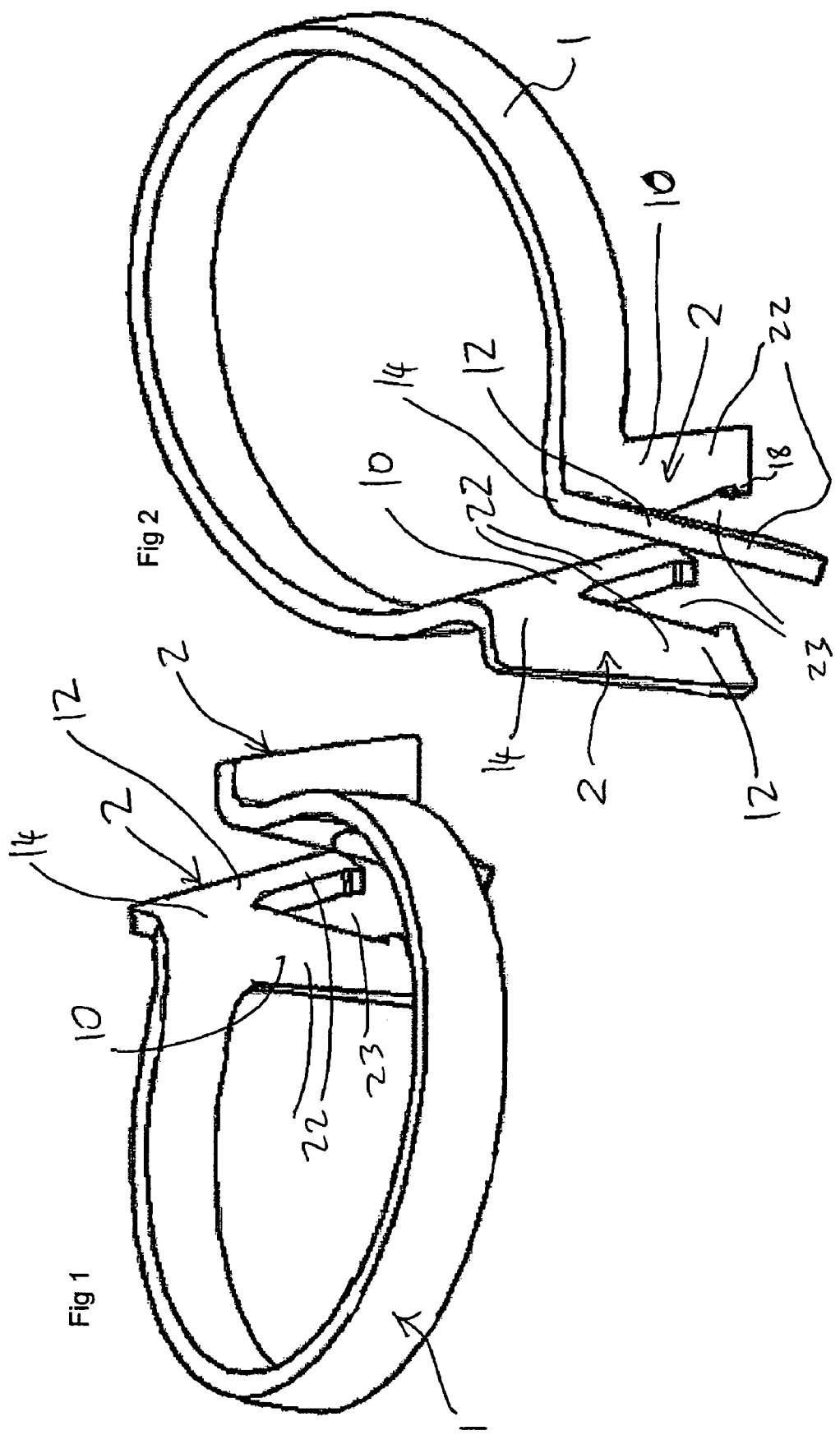

ured tooth.
MATRIX BAND RETAINER

BACKGROUND TO THE INVENTION

1. Field of the Invention

The present invention is in the field of matrix band retainers for use in dental procedures. In particular, the present invention relates to matrix band retainers that are configured to clamp into the interproximal spaces between adjacent teeth to hold a matrix band in proper placement during dental filling procedures.

2. Summary of the Prior Art

In the field of dentistry, dental practitioners often treat patients who have developed cavities in a tooth. In order to treat cavities the dental practitioner removes the infected portion of the tooth and then deposits a filling material such as a composite, a resinous material, or an amalgam into the tooth preparation.

During the dental filling procedure, a matrix band is typically placed against the side of the tooth to approximately define the desired shape of the restored tooth and to keep the filling material from flowing beyond the desired tooth boundary. A matrix band typically comprises a thin metallic or plastic strip that is flexible and can be bent around the tooth being restored. The matrix band is particularly useful because it provides form for the desired shape of the resultant filling. However, if the matrix band is not properly held in place then too much or too little filling material may be deposited into the tooth preparation, thereby distorting the configuration of the restored tooth.

An improper filling can lead to dental discomfort, capture of food particles, infections, and other dental problems. To avoid these problems and to fix a distorted dental filling, it may be necessary to replace the filling. It is desirable, however, to avoid this process because it increases the time and cost of performing the filling procedure and can create anxiety and discomfort for the patient.

In order to place the matrix band into a desired placement, it is sometimes necessary to separate the teeth by placing small dental wedges in the interproximal spaces between the teeth. One inherent problem with the use of matrix bands and dental wedges, however, is that they are susceptible to moving and slipping out from between the teeth. In an attempt to avoid this problem, dental practitioners have used clamps, commonly known as matrix band retainers, to hold the matrix band and dental wedges in place during the filling procedure.

Conventional matrix band retainers consist of a rigid, cylindrical wire bent so as to have a generally circular body and one of two generally straight tines extending perpendicularly from each end of the circular body. During use, the tines are spread open and placed in the interproximal spaces between the tooth being repaired and an adjacent tooth. One problem with such matrix band retainers is that the tines do not anatomically conform to the shape of the teeth. This results in inadequate retention of the matrix band such that the matrix band in an anatomically correct conformation. In addition, some matrix band retainers can easily slip out of position.

Examples of prior art matrix band retainers include U.S. Pat. No. 6,336,810, U.S. Pat. No. 6,220,858 and U.S. Patent Publication 2002/0155410.

U.S. Pat. No. 6,336,810 shows a "flexible open ended ring with top and bottom surfaces, each forming a plane, the ring having two downward extending tines, permanently incorporated into the open ends of the ring, each tine at an obtuse angle from the bottom plane of the ring". The bottom edge of each tine converges toward the other. Each tine is basically a rectangular planar extension from the ring.

U.S. Pat. No. 6,220,858 discloses a clamp 50. "Clamp 50 is generally semi-circular or u-shaped in plane view (FIG. 3A) and has a pair of arms 52 extending in a plane. Arms 52 are under tension and require that force be applied to move them apart. Each arm 52 has a tooth engaging surface 54 thereon. Surfaces 54 are defined by a tine 56 depending outwardly from the plane of the arms. Tine 56 is sized to extend over at least a portion of a tooth about which it is engaged. Tine 56 is bifurcated at its end to form two extensions 57. Extensions 57 defining between a notch 58A, 58B. Notch is formed to be v-shaped so that it fits over the other portion of a wedge such as that wedge shown in Figure A".

U.S. patent application publication 2002/0155410 describes a matrix band retainer in which "the tines may be curved and/or include a wedge shaped portion to facilitate insertion of the tines into the interproximal spaces between two adjacent teeth. The "member 70 and tines 50 and 60 are formed by shaping a single piece of generally rigid wire" and "curvature of tine bodies 56 and 66 is formed by bending tines 50 and 60 during the manufacturing process".

SUMMARY OF THE INVENTION

A matrix band retainer that goes some way towards overcoming the above disadvantages or will at least provide the dental profession with a useful choice.

In a first aspect the invention consists in a matrix band retainer for dental restoration comprising:

a unitary member of a stiff planar spring material formed to have an open ring substantially in a first plane, with the plane of said material of said ring perpendicular to said first plane, a tine at each end of said open ring, each tine extending substantially normal to said plane of said ring, with at least one said tine having a first planar portion extending from the respective end of said ring and a second planar portion extending from said first portion, at an angle to said first portion and adjoining said first portion, to define a ridge, facing the other said tine; the ring, the first planar portion, the second planar portion and the ridge being arranged so that, in use, the first and second planar portions can press against respective first and second adjacent teeth, with said ridge pressing into the interproximal zone between said first and second teeth, and with the other said tine pressing against the opposite side of the same pair of adjacent teeth.

In a further aspect the invention consists in a matrix band retainer for dental restoration comprising a first tooth engagement portion for engaging against one side of a pair of teeth, a second tooth engagement portion for engaging against the other side of said pair of teeth, and a spring member connecting between said first tooth engagement portion and said second tooth engagement portion biasing said portions to a closed condition where said engagement portions are separated by less than the width of a tooth, said first tooth engagement portion and said second tooth engagement portion each comprising a member of low thickness relative to its width and height having a narrow proximal portion connected with said spring and a wider distal portion extending away from said spring and a bend extending from said narrow proximal portion to said wider distal portion, dividing said tooth engagement portion into a first planar portion and a second planar portion and defining a ridge there between, the ridge of said first tooth engagement portion and the ridge of said second tooth engagement portion facing each other across a gap into which said teeth are interposed in use, such that, in use, the first and second planar portions of said first tooth engagement portion press against respective first and second adjacent teeth with said ridge pressing into the interproximal zone between the first and second teeth, and the second tooth engagement portion pressing against the other side of said pair of teeth.

In a still further aspect the invention consists in a method of manufacturing a matrix band retainer comprising the steps of:

forming a blank of a unitary member from a web of stiff planar spring material, said blank including a substantially straight band and a tine portion extending from each end of said band in a direction substantially perpendicular to said band, bending said substantially straight band to form an open ring, and bending said tine portion to form two planar portions adjoined by a ridge extending substantially parallel with said tine and substantially perpendicular to said band.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

FIG. 1 is a perspective view of a matrix band retainer according to the first embodiment of the present invention.

FIG. 2 is a perspective view of the retainer of FIG. 1 shown from another angle.

DETAILED DESCRIPTION

Figure 3:
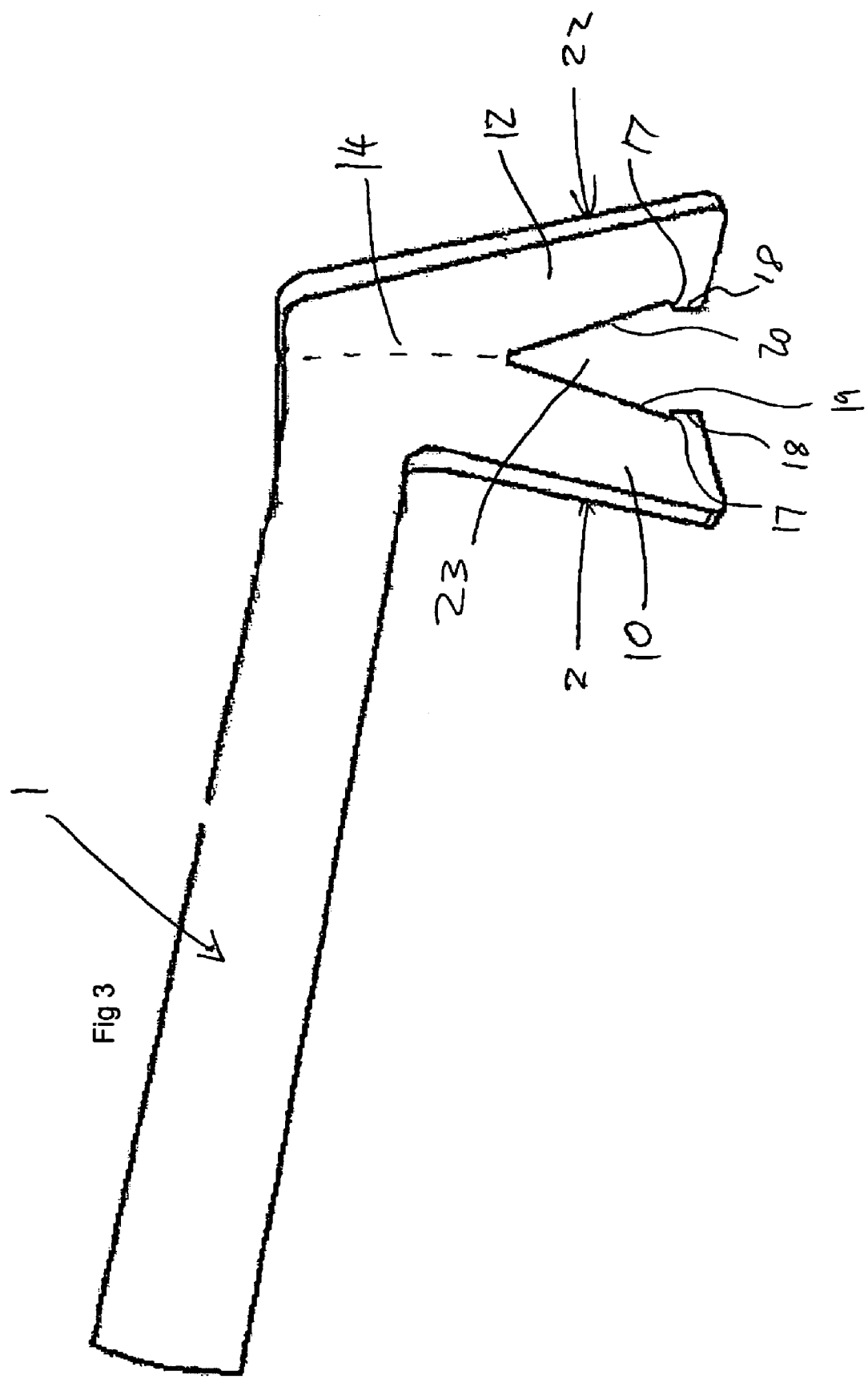
FIG. 3 is a side elevation of one arm and associated tine of the retainer of FIG. 1.

It is an object of this invention to enable a dentist to more easily restore a proximal cavity on a tooth using a matrix band. The device according to the present invention is a matrix band retainer formed of a planar spring material with two faces on each tine. The faces transmit the force of the spring to separate the teeth while holding the sectional matrix in place. Preferably a gap between the faces of each tine facilitates the easy placement of a dental wedge.

Referring to the figures in the preferred embodiment of the present invention the matrix band retainer has a main body of an entirely unitary construction with a circular or overall horseshoe shaped spring 1 with a tine 2 at each end. The spring 1 is essentially an open ring. It does not necessarily follow a circular, oval or horseshoe path. Other curvilinear forms could be used. However a substantially circular or horseshoe ring is preferred for providing a combination of open access to the tooth biting surface and relative compactness.

In one embodiment of the present invention described later with reference to FIGS. 6 to 8 the spring effect of the open ring unitary member is supplemented by an additional spring member.

Referring to both embodiments, each tine 2 preferably has two distinct legs 22. In the preferred form, the retainer is designed to accommodate a wedge. A space 23 is provided between the legs, separating the ends of the legs that are directed away from the circular spring 1. This end of each leg will hereafter be referred to as the distal end of the leg. The other end of the legs, the proximal end, are adjoined to one another and to the free ends of the ring.

The tine of the preferred embodiments of the invention includes generally a pair of planar portions, for example portion 10 and portion 12. One of these planar portions (portion 10) extends directly from an end of the ring, while the other planar portion 12 continues from the first planar portion 10, at an angle to the first planar portion 10, thereby defining a joining ridge 14. So each tine comprises a pair of planar portions arranged at an angle to one another and adjoined along a ridge. In the preferred form the tine also includes space 23 and each planar portion is associated with one of the legs of the tine, so each planar portion is separated at least along a distal portion by the gap or space 23 to accommodate a wedge.

Figure 5:
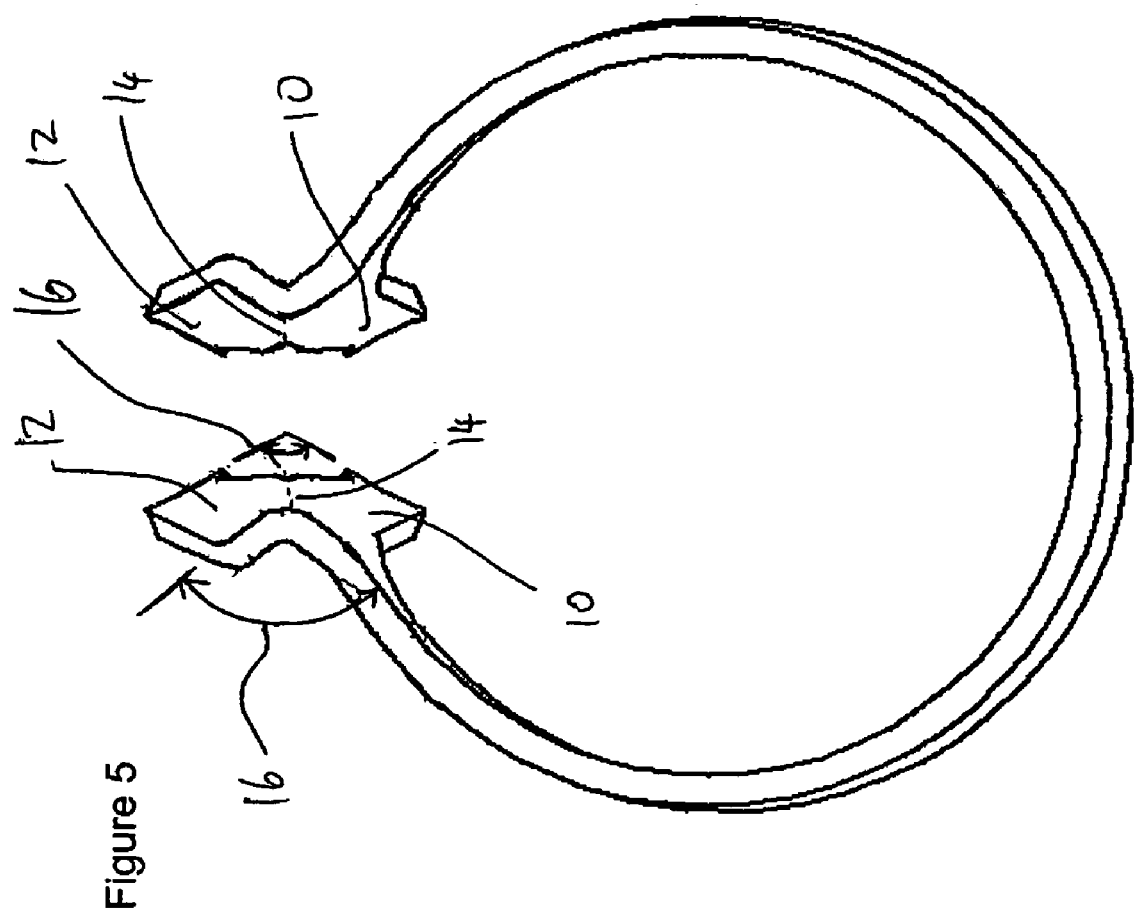
FIG. 5 is a plan elevation of the retainer of FIG. 1.

The arrangement of the two planar portions is chosen so as to conform as far as possible to the interproximal area of a pair of teeth to allow the tine to grip on the bulbous sites of the neighbouring teeth either side of the embrasure that contains the tooth to be restored. In respect of the tine this is essentially a function of the angle 16 between the planar portions. As illustrated in FIG. 5, the angle 16 between the legs is preferably within the range of approximately 65° to 130°. This is the angle included by the surfaces when viewed in plan. Due to the stiffness of the material which is preferably used for constructing the unitary member of the device each retainer will typically have only a single possible configuration within this range. For example the portions will have a relative angle within the range 65° to 130°.

It may be useful to have a range of devices in accordance with the invention, the range of devices providing a number of options of different relative angles.

It may also be possible to provide a device according to the present invention where the user bends one portion relative to the other portion (bending occurring at the line of the ridge) to adopt a desired configuration. While that would be possible, the preferred materials for implementing the present device suggest that it would not be a particularly practical approach to implementing the invention. The preferred material (stainless steel or nickel titanium alloy spring materials) has very high elastic yield points. Generally the devices are not intended to be single use.

In any case the inventor has found that a device with an angle between the planar portions of around 82° and formed in accordance with the embodiment of FIGS. 6 to 9 has worked effectively, and has worked across most oral situations.

In addition to the planar portions of each tine being at an angle to one another the general disposition of each tine is also at an angle to the other tine. In particular the ridges of the tines converge extending toward the wedge receiving space. This convergence is best illustrated in FIG. 5 where it can be seen that the distance between the top end of each ridge 14 is substantially greater than the distance between the lower end of each ridge adjacent the wedge receiving space 23.

In each tine the wedge receiving space 23 is preferably an open bottomed substantially triangular opening. It is preferred that this open bottomed triangular opening is of sufficient depth or height (the separated portion of the legs of the tine are sufficiently long) that the legs extend beyond and below the wedge with the wedge and retainer in place. This arrangement is illustrated, by way of example, in FIG. 4.

With this arrangement it is preferred to provide each leg of the tine, or at least one leg of the tine, with a feature to help secure the dental wedge. This feature is preferably on the inward facing edge 19 or 20 defining the space 23, and is for engaging against an edge of a triangular dental wedge, so that the retainer can further support the dental wedge in its inserted position. In the preferred form the inside edge 19 and 20 of each leg 22 has a small ledge 17 formed on a protruding toe 18. The lower edges of the triangular dental wedge are engaged by the ledge of the respective toe.

As can also be seen in the drawings the preferred tine also has a general flare extending to its distal end. Overall the tine is narrower between its outside edges at the upper end adjacent the ring than at the lower or distal end. The wide planar forms of the tine mean that the tine itself is also somewhat flexible in use. Furthermore the width and flare allows the tine to span the cavity being repaired, even where the interproximal space is rather wide. Although the tines are wide, they are also comparatively thin (0.7 mm to 1.1 mm material thickness) so the tine does not compromise access to the tooth for work by the dentist, or for placement of the wedge.

The most preferred form of the present invention, including the most preferred form of the tines, is illustrated in FIGS. 6 to 9. In that embodiment, the tines flare outwards so that in overall form the tines are narrower at the top or proximal end and wider at the bottom. The distal end of each tine is also slightly bent so that the tooth engaging faces of the tines are slightly concave. Preferably each tine is substantially symmetric about the ridge line 14, each leg of the tine being substantially the same form and configuration and facing the other leg across the ridge line. Preferably each tine is also a mirror image of the other tine so that the tines are symmetric across the separating gap between them.

In the closed condition of the retainer this separating gap may be as small as for example 0.6 mm. In an open position for application to the teeth this gap will typically be around 5 mm to 8 mm. It can be seen in FIG. 8 that in the closed position the planar portions 10 form an angle between them that is larger than the angle between the planar portions 11. This is so that when the retainer is manipulated into the open position these angles are substantially the same.

By way of general example, in the preferred embodiment of the retainer illustrated in FIGS. 6 to 9 the overall dimensions of the ring are such as to have a width of approximately 20 mm and a length of approximately 25 mm. The overall height of the retainer (with the tines aligned vertical) from the top of the ring to the bottom faces of the tines is approximately 14 mm. The tines extend approximately 6 mm from the bottom of the ring (adjacent each tine). Each tine is approximately 5.5 mm width overall at its distal end and approximately 3.5 mm width overall at its upper end. The triangular opening for receiving the wedge is approximately 3.5 mm across above the toes and the gap between the toes is approximately 3 mm. The triangular opening is approximately 3.5 mm deep.

Figure 4:
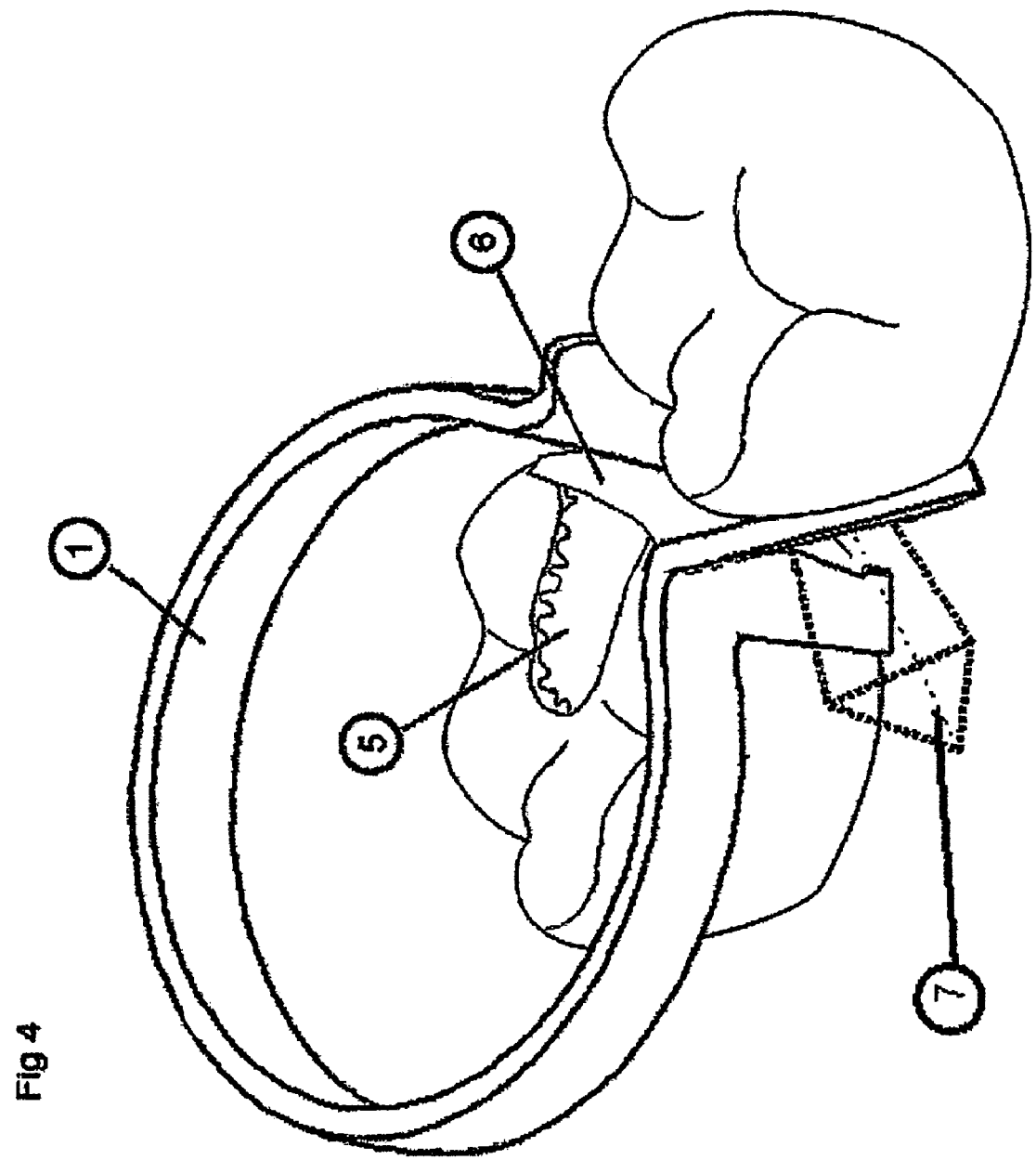
FIG. 4 is a perspective view of the retainer of FIG. 1 in use holding a matrix band against a prepared tooth. A triangular dental wedge is depicted in phantom.

FIG. 4 shows the device in position. The device straddles the interproximal space between two teeth. This drawing shows a class 2 cavity 5 and a sectional matrix 6 held in place by the opposed planar portions 10. FIG. 4 also shows the position of the wedge 7 in place through the space 23. The wedge 7 can be inserted into or removed from the space 23 between the legs of the tines without having to remove the device. To some extent the retainer and the wedge become mutually assembled once the matrix band retainer according to the present invention is fitted onto the teeth. The wedge may be inserted after the retainer is fitted to the teeth. The wedge may be inserted after the retainer is fitted to the teeth.

Preferably, as with prior art devices, the tines extend from the ring shaped spring at an angle not entirely perpendicular to the spring, so that when the tines essentially vertical on the teeth the arm of the spring slants upward. This slight angle improves access to the teeth and allows multiple retaining members to be used in close proximity with the rings overlapping.

Referring now specifically to the embodiment of FIGS. 1 to 4 the device is preferably constructed as a single unitary member, preferably from an alloy of titanium, such as nickel titanium. Alternatively the device may be formed from stainless steel. In either case the device is preferably formed from a rolled sheet material, which may be cut from the sheet as a planar blank and then bent into shape.

Figure 6:
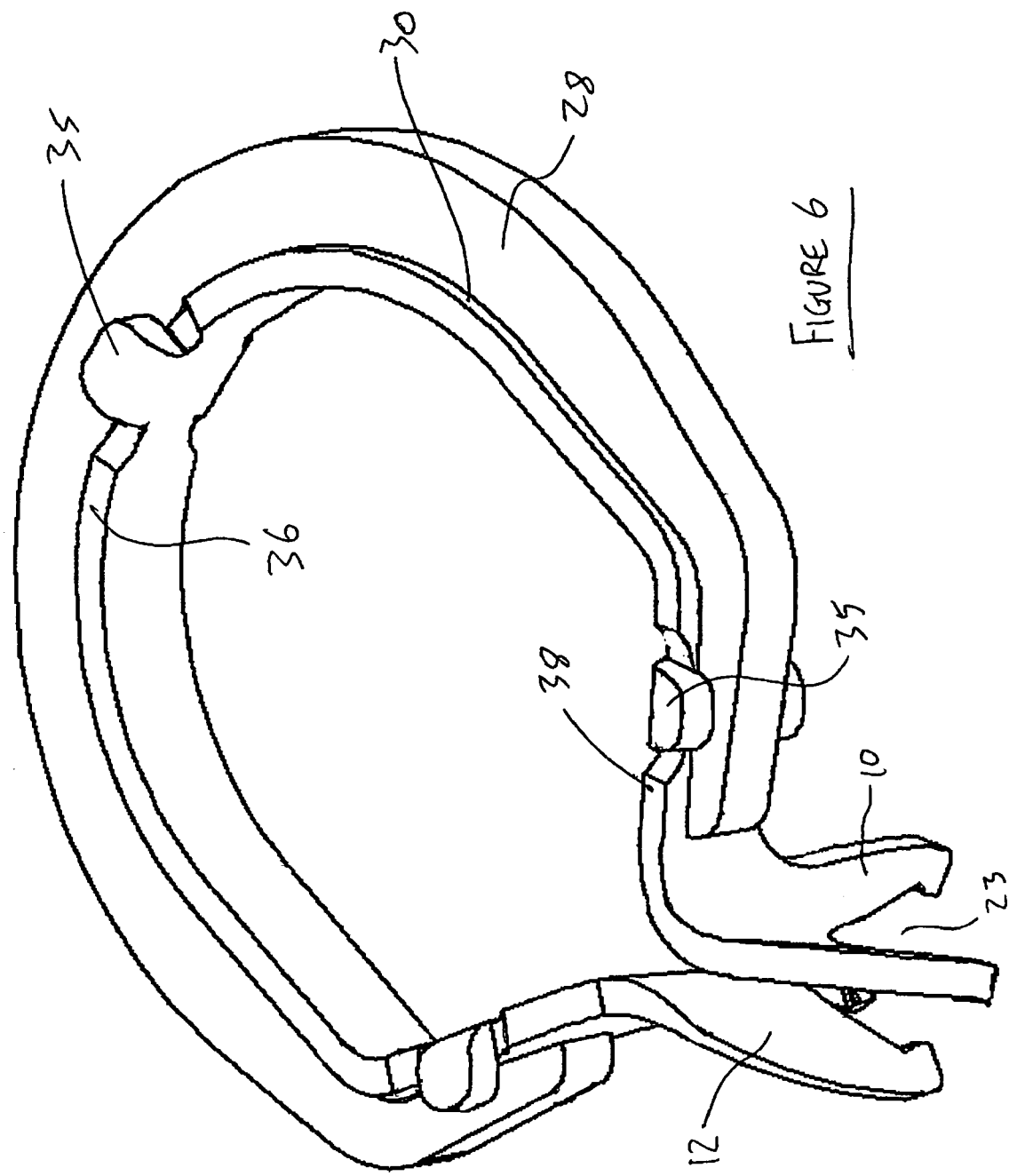
FIG. 6 is a perspective view of a matrix band retainer according to an alternate embodiment of the present invention in which the retainer includes a separate spring member.
Figure 7:
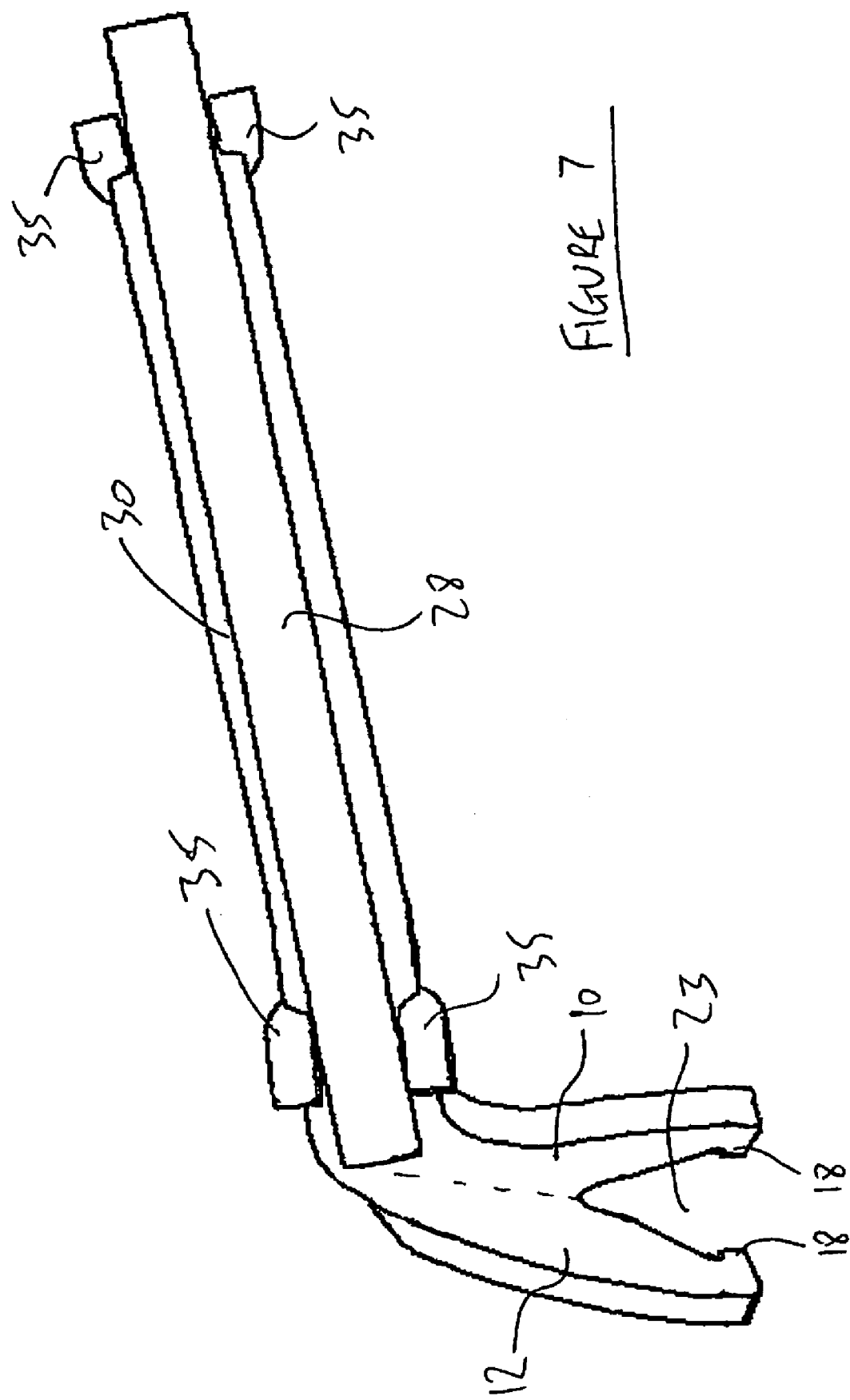
FIG. 7 is a side elevation of one arm and associated tine of the retainer of FIG. 6.
Figure 8:
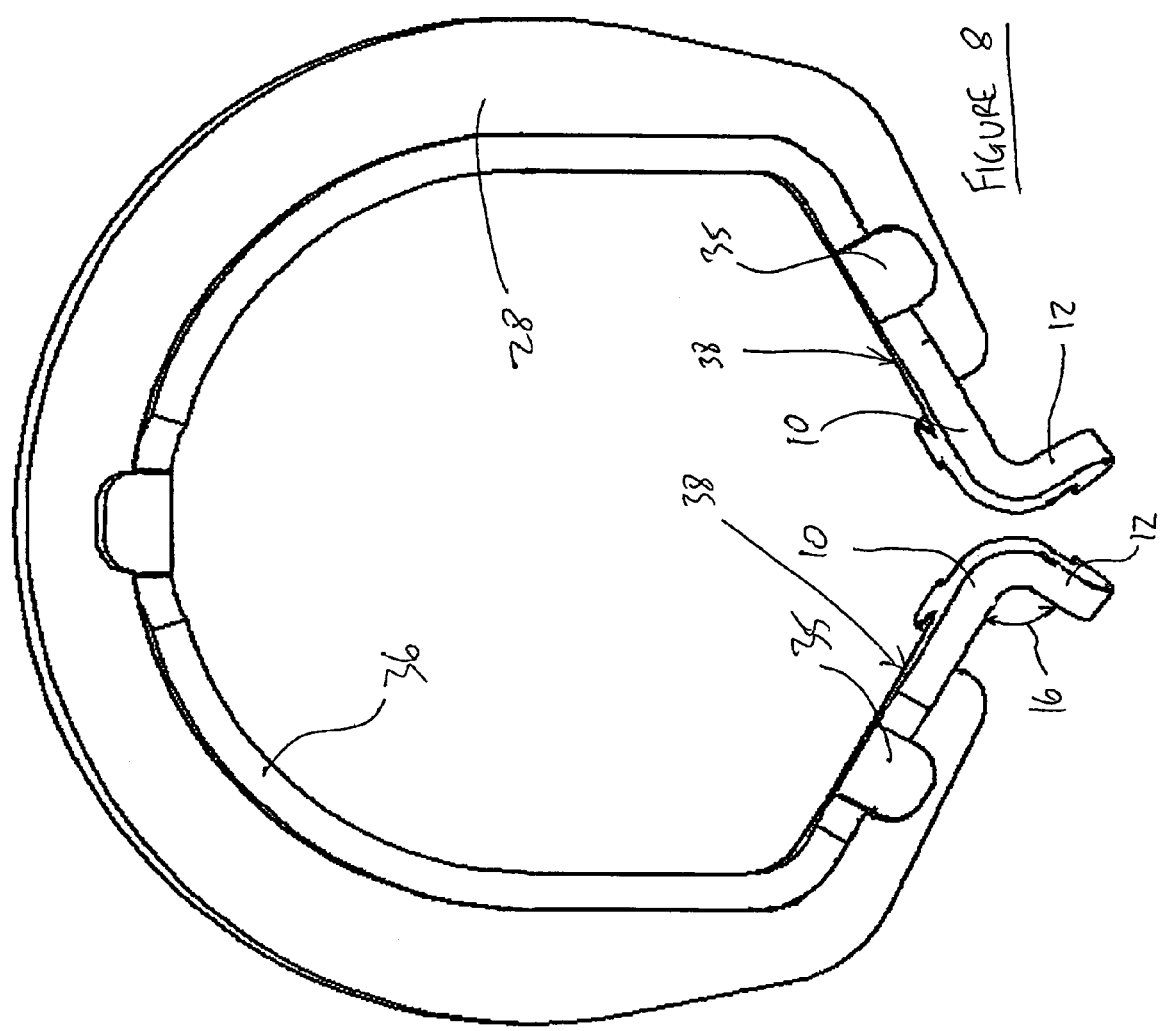
FIG. 8 is a plan elevation of the retainer of FIG. 6.

The embodiment of FIGS. 6 to 8 recognises that additional spring strength may be required where the thin sheet material which is best for making the planar type tines is then not inherently sufficiently stiff and strong to provide the spring force desired against the teeth. In that case an additional spring member may supplement the spring effect of the ring portion of the retainer. In the preferred embodiment the additional spring member is a separate component rib 28 shaped to match the peripheral plan form shape of the outer surface 30 of the ring. The rib member 28 is fitted over the ring, and is held in place by a set of bent tabs 35. Pairs of bent tabs are provided at a number of spaced apart locations. Ideally the number of spaced apart locations is at least three. The tabs may be bent into place after the rib member is fitted to the ring. Alternatively the rib member may be expanded (remaining in elastic defamation) to be fitted past the tabs.

The arrangement of FIGS. 6 to 8 provides for a larger spring force than would be normally associated with the thickness of material of the tines (if that where the basis only for the spring) while retaining a low profile height for the ring. Access to the biting surface of the tooth is compromised more by raising the height profile of the ring than by expanding its width.

Figure 9:
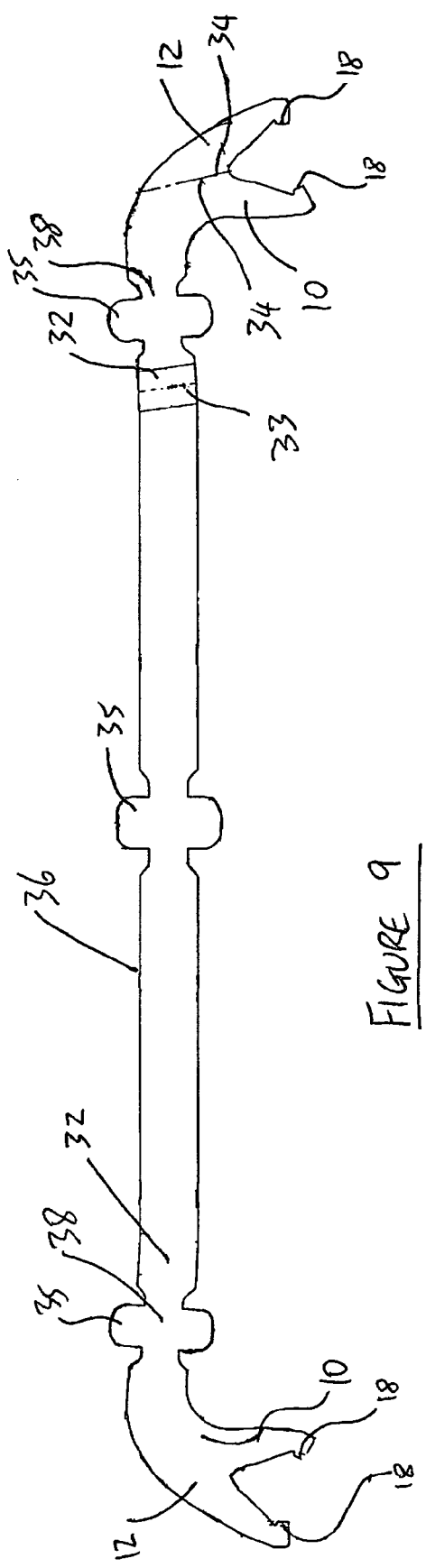
FIG. 9 is a plan elevation of a blank for forming the unitary member part of the retainer of FIG. 6.

A blank for the unitary member part of the device of FIG. 6 is illustrated in FIG. 9. This illustrates certain features that indicate the alignment of the parts of the device when bent up into the final form. For example the long straight member bends into a substantial loop to become the spring portion of the ring. This main straight portion 36 is linked at either end to two arm portions 38. These arm portions 38 remain practically linear in the formed device. A kink portion 32 is provided between each arm portion 38 and the main straight portion 36. Each kink portion 32 is bent on a line (for example line 33) angled to both the straight portion 36 and the arm 38, to provide angular transition between the ring and the arms. The transition contributes to the ring being slanted when the tines are substantially vertical, and contributes to the convergent slant of the first planar portion 10, of each tine.

The first planar portion 10 of each tine remains substantially co-planar with the plane of the respective arm portion. The tine is bent substantially along the center line 34 through the preferred angle (for example 82°) so that the planar portions 10, 12 extend away from ridge 14 in the finished retainer.

So the unitary member is prepared from the blank by bending the main ring portion to shape and by bends at each of the two kink portions and down the center line of each tine. The tabs 35 can either be bent into position before or after fitting the additional spring member.

Preferably each leg of each tine is also flared outward toward its distal end. For example the distal portion of each planar portion may be bent toward the other tine through a small angle (such as 3°) relative to the proximal part of planar portion, and the ultimate end, the toe portion, through an additional angle (such as to be 14° to the proximal part of the planar portion). Accordingly the planar portions are only substantially planar, and are preferably actually be slightly concave on their tooth engaging faces.

The advantages of this device over the prior art are that:

1. The device does not tend to slip between the teeth when the cavity is wide, as occurs with previous matrix spring retainers.

2. The triangular gap 2 between the legs of each tine allows room for the wedge to be placed. With this new device, the wedge can either be placed after the spring retainer has been positioned, or the wedge can be placed first and then the device can be fitted.

I claim:

1. A matrix band retainer for dental restoration comprising:
    a unitary member of a stiff planar spring material formed to have an open ring substantially in a first plane, with the plane of said material of said ring perpendicular to said first plane, a tine at each end of said open ring, each tine extending substantially normal to said plane of said ring, with at least one said tine having a first portion of said planar material extending from the respective end of said ring and a second portion of said planar material extending from said first portion, at an angle to said first portion and adjoining said first portion, to define on one side a ridge, facing the other said tine, and on the other side a valley facing away from the other said tine;
    the ring, the first portion of said planar material, the second portion of said planar material and the ridge being arranged so that, in use, the first and second portions of said planar material can press against respective first and second adjacent teeth, with said ridge pressing into the interproximal zone between said first and second teeth, and with the other said tine pressing against the opposite side of the same pair of adjacent teeth.

2. The matrix band retainer as claimed in claim 1 wherein said first portion of said planar material and said second portion of said planar material define an angle behind said ridge of 65° to 130°, the angle defined in a plane parallel to the plane of said ring.

3. The matrix band retainer as claimed in claim 2 wherein said angle behind said ridge is approximately 80°.

4. The matrix band retainer as claimed in claim 2 wherein said stiff planar spring material is between 0.7 mm and 1.1 mm thick.

5. A matrix band retainer for dental restoration comprising:
    a unitary member of a stiff planar spring material formed to have an open ring substantially in a first plane, with the plane of said material of said ring perpendicular to said first plane, a tine at each end of said open ring, each tine extending substantially normal to said plane of said ring, with at least one said tine having a first planar portion extending from the respective end of said ring and a second planar portion extending from said first portion, at an angle to said first portion and adjoining said first portion, to define a ridge facing the other said tine; said first planar portion and said second planar portion defining an angle behind said ridge of 65° to 130°, the angle defined in a plane parallel to the plane of said ring; and the tine being bifurcated at the end distal from said ring, such that a distal portion of said first planar portion and a distal portion of said second planar portion are divided by a notch,
    the ring, the first planar portion, the second planar portion and the ridge being arranged so that, in use, the first and second planar portions can press against respective first and second adjacent teeth, with said ridge pressing into the interproximal zone between said first and second teeth, and with the other said tine pressing against the opposite side of the same pair of adjacent teeth.

6. The matrix band retainer as claimed in claim 5 wherein each said tine is a mirror of the other.

7. The matrix band retainer as claimed in claim 6 wherein each said tine flares outward as it extends away from said ring.

8. The matrix band retainer as claimed in claim 7 wherein each said planar portion is sloped outward moving toward its distal end from the ring end so that the defined ridge converges toward the other tine moving toward the distal end.

9. The matrix band retainer as claimed in claim 6 wherein each of said first planar portion and said second planar portion is slightly concave on the outside face thereof.

10. The matrix band retainer as claimed in claim 6 wherein said first planar portion is substantially coplanar with the adjacent end portion of said ring.

11. The matrix band retainer as claimed in claim 6 wherein, when said matrix band retainer is in a rest condition the angle between the first planar portion of one tine and the first planar portion of the other tine is larger than the angle between the second planar portion of the first tine and the second planar portion of the other tine, but with the ring opened to an in-use condition the angle between the first planar portions is substantially the same as the angle between the second planar portions.

12. The matrix band retainer as claimed in claim 6 including a backing spring member secured around the outside of said ring of said unitary member such that at least with the ring expanded in use the outer ring member contributes to the clamping force pushing or pressing the tines together.

13. The matrix band retainer as claimed in claim 12 wherein said backing spring member is located around said unitary member by a plurality of tabs bent outward from said ring.

14. The matrix band retainer as claimed in claim 5 wherein said notch is substantially triangular, being defined by an edge of said distal portion of said first portion, an edge of said distal portion of said second portion and the line between the distal end of said first portion and the distal end of said second portion.

15. The matrix band retainer as claimed in claim 14 wherein said first planar portion includes an inward toe adjacent said distal end, extending from said edge of said first distal portion generally toward said second planar portion, and said second planar portion includes an inward toe adjacent said distal end extending from said edge of said second distal portion substantially toward said first distal portion.

16. The matrix band retainer as claimed in claim 5 wherein said angle behind said ridge is approximately 82°.

17. The matrix band retainer as claimed in claim 5 wherein said stiff planar spring material is between 0.7 mm and 1.1 mm thick.

18. A matrix band retainer for dental restoration comprising a first tooth engagement portion for engaging against one side of a pair of teeth, a second tooth engagement portion for engaging against the other side of said pair of teeth, and a spring member connecting between said first tooth engagement portion and said second tooth engagement portion biasing said portions to a closed condition where said engagement portions are separated by less than the width of a tooth, said first tooth engagement portion and said second tooth engagement portion each comprising a member of low thickness relative to its width and height having a narrow proximal portion connected with said spring and a wider distal portion extending away from said spring and a bend extending from said narrow proximal portion to said wider distal portion, dividing said tooth engagement portion into a first planar portion and a second planar portion and defining a ridge there between, the ridge of said first tooth engagement portion and the ridge of said second tooth engagement portion facing each other across a gap into which said teeth are interposed in use, such that, in use, the first and second planar portions of said first tooth engagement portion press against respective first and second adjacent teeth with said ridge pressing into the interproximal zone between the first and second teeth, and the second tooth engagement portion pressing against the other side of said pair of teeth.

19. The matrix band retainer as claimed in claim 18 wherein said thickness is between 0.7 mm and 1.1 mm.

20. The matrix band retainer as claimed in claim 19 wherein said first planar portion and said second planar portion define an angle of approximately 82°.

21. The matrix band retainer as claimed in claim 20 wherein each said tooth engagement portion is bifurcated, with a distal portion of said first planar portion and a distal portion of said second planar portion being separated by a substantially triangular open notch.

* * * * *